(12) United States Patent
Koide et al.

(10) Patent No.: US 6,268,527 B1
(45) Date of Patent: Jul. 31, 2001

(54) METHOD FOR PRODUCING BENZOIC ACID DERIVATIVES

(75) Inventors: Makoto Koide; Michio Ishida, both of Saitama; Yuzuru Morino; Seiji Hasegawa, both of Yamaguchi; Satoru Narizuka; Takashi Kume, both of Saitama, all of (JP)

(73) Assignee: Central Glass Company, Limited, Ube (JP)

( * ) Notice: Subject to any disclaimer, the term of this patent is extended or adjusted under 35 U.S.C. 154(b) by 0 days.

(21) Appl. No.: 09/452,945

(22) Filed: Dec. 2, 1999

(30) Foreign Application Priority Data

Dec. 2, 1998 (JP) .................................................. 10-343402

(51) Int. Cl.⁷ .................................................. C07C 51/10
(52) U.S. Cl. ........................... 562/406; 560/103; 562/493
(58) Field of Search ..................... 562/406, 493; 560/103

(56) References Cited

FOREIGN PATENT DOCUMENTS

| 64-47 | 1/1989 | (JP) . |
| 9-67297 | 3/1997 | (JP) . |

OTHER PUBLICATIONS

Lichtenberger, J., and Weiss, F. (1962) "Sur les dérivés du phenylfluoroforme. I. –Les trifluoromethyl–benzophenones" *Bull. Soc. Chim.* France p. 587–593.

Makhaev, V.D., Dzhabieva, Z.M., Konovalikhin, S.V., D'yachenko, O.A., and Belov, G.P. (1996) "The Crystal and Molecular Structure of [1,4–Bis(diphenylphosphino)butane] palladium (II) Dichloride". *Russian J. Coord, Chem. (Engl. Edit.)* 22:563–567.

Chem. Abst. 126: 277273 (1997).*

* cited by examiner

*Primary Examiner*—Paul J. Killos
(74) *Attorney, Agent, or Firm*—Crowell & Moring, L.L.P.

(57) ABSTRACT

The invention relates to a method for producing a benzoic acid derivative represented by the general formula (1). The method includes the step of reacting an aromatic compound represented by the general formula (2), with carbon monoxide and a hydroxy compound (i.e., water or an alcohol), in the presence of (a) a metal compound containing a metal of 8, 9 and 10 groups of periodic table, (b) a first phosphine derivative represented by the general formula $(R^1)_2P-Q-P(R^1)_2$, and (c) a base,

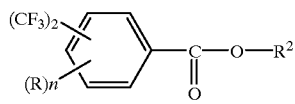

(1)

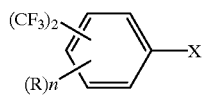

(2)

It is possible to easily and efficiently produce the benzoic acid derivative by the method.

22 Claims, No Drawings

METHOD FOR PRODUCING BENZOIC ACID DERIVATIVES

BACKGROUND OF THE INVENTION

The present invention relates to a method for producing benzoic acid derivatives, each having at least two trifluoromethyl groups on the benzene ring, which are useful as intermediates of medicines, agricultural chemicals and various functional materials, and a novel compound obtained by this method.

Japanese Patent First Publication JP-A-64-47 discloses a method for producing a carboxylic acid. In this method, an organic chloride having at least one chlorine atom on its ring is reacted with carbon monoxide at a temperature of 150–300° C. in the presence of a base, using a palladium compound and a phosphine compound (e.g., bis(diphenylphosphino)butane) as catalysts.

Bull. Soc. Chim. France (1962) 587–93 discloses a method for producing 3,5-bis(trifluoromethyl)benzoic acid from 3,5-bis(trifluoromethyl)bromobenzene by Grignard reaction.

JP-A-9-67297 discloses a method for producing 3,5-bis(trifluoromethyl)benzoic acid and its ester. In this method, a starting material, 3,5-bis(trifluoromethyl)bromobenzene, is reacted with carbon monoxide and water or methanol in the presence of triethylamine and a catalyst that is a combination of palladium acetate and triphenylphosphine.

SUMMARY OF THE INVENTION

It is possible to obtain 3,5-bis(trifluoromethyl)benzoic acid and its ester with relatively good selectivity and yield by the method of JP-A-9-67297. In this method, however, some of the palladium may deposit in the form of palladium black, when it is started to introduce carbon monoxide into the reaction system. This may result in the actual decrease of the catalyst concentration. Therefore, it may be necessary to use a relatively large amount of the palladium compound. In the reaction of this publication, the halogen atom on the benzene ring of the starting material may be replaced with hydrogen atom, thereby producing a by-product. With this, the yield may become inferior. Furthermore, it may be difficult to separate such by-product from the aimed product.

It is therefore an object of the present invention to provide a method for producing a bis(trifluoromethyl)benzoic acid derivative in an easy, efficient way.

It is another object of the present invention to provide a novel bis(trifluoromethyl)benzoic acid derivative.

According to the present invention, there is provided a method for producing a benzoic acid derivative represented by the general formula (1). This method comprises reacting an aromatic compound represented by the general formula (2), with carbon monoxide and a hydroxy compound represented by the general formula (3), in the presence of (a) a metal compound containing a metal of 8, 9 and 10 groups of periodic table, (b) a first phosphine derivative represented by the general formula (4), and (c) a base,

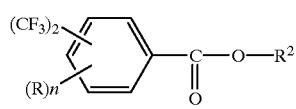
(1)

where R is trifluoromethyl group, trifluoromethyloxy group, a halogen that is fluorine, chlorine, bromine or iodine, nitro group, acetyl group, cyano group, an alkyl group having a carbon atom number of 1–4, an alkoxyl group having a carbon atom number of 1–4, or an alkoxycarbonyl group having a carbon atom number of 2–5; $R^2$ is hydrogen or an alkyl group having a carbon atom number of 1–10; and n is an integer of 0–3,

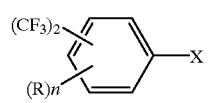
(2)

where X is a halogen as defined above, trifluoromethanesulfonate group, an alkylsulfonate group having a carbon atom number of 1–4, or a substituted or unsubstituted arylsulfonate group; and R and n are defined as above, $$R^2OH \tag{3}$$

where $R^2$ is defined as above,

(4)

where each $R^1$ is independently phenyl group, o-methylphenyl group, m-methylphenyl group, or p-methylphenyl group; and Q is a bivalent group.

According to the present invention, there is provided a novel bis(trifluoromethyl)benzoic acid derivative, that is, 2-chloro-3,5-bis(trifluoromethyl)benzoic acid, made by the method of the invention.

DESCRIPTION OF THE PREFERRED EMBODIMENTS

In the invention, as will be clarified hereinafter, the yield and the selectivity can be remarkably improved by using a palladium compound as the above metal compound together with the above special phosphine derivative. Furthermore, it is possible to significantly reduce the deposition of the metal (e.g., palladium) by using as the metal compound the after-mentioned complex compound such as dichloro[1,4-butanediylbis(diphenylphosphine)P,P']palladium, $PdCl_2$ (dppb).

As stated above, the aromatic compound, which is the starting material of the invention, is represented by the general formula (2). In this formula, R is not particularly limited as long as it is an inert substituent in the reaction. In fact, as mentioned above, R can be trifluoromethyl group, trifluoromethyloxy group, a halogen that is fluorine, chlorine, bromine or iodine, nitro group, acetyl group, cyano group, an alkyl group having a carbon atom number of 1–4, an alkoxyl group having a carbon atom number of 1–4, or an alkoxycarbonyl group having a carbon atom number of 2–5. Examples of the alkyl group are methyl group, ethyl group, n-propyl group, and i-propyl group. Examples of the alkoxyl group are methoxy group, ethoxy group, n-propoxy group, and i-propoxy group. Examples of the alkoxycarbonyl group are methoxycarbonyl group, ethoxycarbonyl group, n-propoxycarbonyl group, and i-propoxycarbonyl group. In the general formula (2), X is the most preferably bromine or iodine in practice. Furthermore, R is preferably chlorine, bromine, or iodine in view of the usefulness of the reaction product as an intermediate in the field of fluorine chemistry.

In the invention, the aromatic compound is preferably a halogeno-bis(trifluoromethyl)benzene represented by the general formula (5),

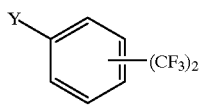

(5)

where Y is bromine or iodine. This halogeno-bis (trifluoromethyl)benzene is not particularly limited. Its nonlimitative examples are
1-bromo-2,4-bis(trifluoromethyl)benzene,
1-iodo-2,4-bis(trifluoromethyl)benzene,
1-bromo-3,5-bis(trifluoromethyl)benzene
[3,5-bis(trifluoromethyl)bromobenzene],
1-iodo-3,5-bis(trifluoromethyl)benzene
[3,5-bis(trifluoromethyl)iodobenzene],
2-bromo-1,3-bis(trifluoromethyl)benzene,
2-iodo-1,3-bis(trifluoromethyl)benzene,
2-bromo-1,4-bis(trifluoromethyl)benzene,
2-iodo-1,4-bis(trifluoromethyl)benzene, and
4-bromo-1,2-bis(trifluoromethyl)benzene.

Similar to the halogeno-bis(trifluoromethyl)benzene, the aromatic compound, which is represented by the general formula (2) and has the substituent R, is also preferably used in the invention. Nonlimitative examples of such aromatic compound are 1-bromo-2,3,4-tris(trifluoromethyl)benzene, 1-bromo-2,4,5-tris(trifluoromethyl)benzene, 1-iodo-2,3,5-tris(trifluoromethyl)benzene, 1-iodo-2,4,5-tris(trifluoromethyl)benzene, 2-bromo-1,3,5-tris(trifluoromethyl)benzene, 5-bromo-1,2,3-tris(trifluoromethyl)benzene, 5-iodo-1,2,3-tris(trifluoromethyl)benzene, 2-iodo-1,3,4,5-tetrakis(trifluoromethyl)benzene, 1,2-dibromo-3,4,5-tris(trifluoromethyl)benzene, 1,3-dichloro-5-iodo-2,4-bis(trifluoromethyl)benzene, 1,2-dibromo-4,5-bis(trifluoromethyl)benzene, 1,4-dibromo-2,5-bis(trifluoromethyl)benzene, 1-bromo-2-chloro-3,5-bis(trifluoromethyl)benzene [2-chloro-3,5-bis(trifluoromethyl)bromobenzene], 1-bromo-2-methoxy-3,5-bis(trifluoromethyl)benzene, 1-iodo-2-methoxy-3,5-bis(trifluoromethyl)benzene, 2-bromo-1-iodo-3,5-bis(trifluoromethyl)benzene, 2-bromo-1-nitro-3,5-bis(trifluoromethyl)benzene, 2-bromo-3,4-dichloro-1,5-bis(trifluoromethyl)benzene, and 5-bromo-2-chloro-1,3-bis(trifluoromethyl)benzene. Of the above examples of the aromatic compound, it is particularly preferable to use 3,5-bis(trifluoromethyl)bromobenzene or 3,5-bis(trifluoromethyl)iodobenzene. With this, it is possible to obtain a 3,5-bis(trifluoromethyl)benzoic acid derivative that is very useful. Furthermore, it is particularly preferable to use 2-chloro-3,5-bis(trifluoromethyl)bromobenzene as the aromatic compound. With this, it is possible to obtain 2-chloro-3,5-bis(trifluoromethyl)benzoic acid derivative that is also very useful.

As stated above, it is possible in the invention to obtain the benzoic acid derivative represented by the general formula (1) by the reaction of the aromatic compound represented by the general formula (2). In this reaction, X of the general formula (2) turns into a carboxyl or alkoxycarbonyl group, but lo the substituent R remains unreacted. As defined above, each of X and R can be a halogen that is fluorine, chlorine, bromine or iodine. In general, different halogen atoms on a benzene ring of an aromatic compound can be arranged in a descending order of iodine, bromine, chlorine and fluorine by reactivity. For example, if an aromatic compound has bromine and chlorine on its benzene ring, the bromine can be more reactive than the chlorine. Thus, it is possible to use as the aromatic compound 2-chloro-3,5-bis (trifluoromethyl)bromobenzene, in which X and R are respectively bromine and chlorine, in order to obtain the aimed 2-chloro-3,5-bis(trifluoromethyl)benzoic acid. The descending order of the halogen atoms may, however, be changed depending on the type of other (optional) groups and their positions on the benzene ring.

In the invention, it is necessary to conduct the reaction in the presence of a metal of 8, 9 and 10 groups of periodic table and a first phosphine derivative represented by the general formula (4). This metal can be selected from iron, cobalt, palladium, platinum, rhodium, ruthenium, iridium, and osmium. Of these, palladium is particularly preferable. In the reaction, it is possible to use this metal in elemental form.

Alternatively, the metal can be carried on a carrier (e.g., graphite, silica gel, alumina, silica-alumina, and molecular sieve). Furthermore, the metal can be used in the form of metal compound, such as metallic salt, in place of elemental form. Examples of this metallic salt are acetates, carbonates, nitrates, chlorides, bromides and coordination compounds having solvent molecules as a ligand. Concrete examples of the metallic salt are palladium acetate, palladium chloride, palladium bromide, cobalt acetate, cobalt carbonate, cobalt chloride, ruthenium bromide, $PdCl_2$(acetonitrile)$_2$ and $PdCl_2$(benzonitrile)$_2$.

In the invention, the metal compound can be a complex compound represented by the general formula (6), $$(L^1)_b(L^2)_aM \qquad (6)$$

where $L^1$ is a second phosphine derivative represented by the general formula (4) or a third phosphine derivative represented by the general formula (7); $L^2$ is a ligand selected from the group consisting of chlorine, bromine, iodine, S, NO, CO, $CH_3COO-$, cyclopentadienyl, cyclooctadiene, and diphenylacetylene; M is a metal of 8, 9 and 10 groups of periodic table; the total of "a" and "2b" equals to coordination number of "M" when $L^1$ is a bidentate ligand; and the total of "a" and "b" equals to coordination number of "M" when $L^1$ is a monodentate ligand,

(4)

where $R^1$ and Q are defined as above, $$P(L)_3 \qquad (7)$$

where each L is independently a lower alkyl group, phenyl group, or a substituted phenyl group having a lower alkyl substituent. Examples of the second and third phosphine derivatives are 1,1'-bis(diphenylphosphino)ferrocene (dppf), 1,4-bis(diphenylphosphino)butane (dppb), 1,3-bis(diphenylphosphino)propane (dppp), 1,2-bis(diphenylphosphino)ethane (dppe), triphenylphosphine, tri-o-tolylphosphine, tri-m-tolylphosphine, tri-p-tolylphosphine, tri-n-butylphosphine, and triethylphosphine. First examples of the complex compound represented by the general formula (6) are $PdCl_2[P(Ph)_2CH_2CH_2P(Ph)_2]$, $PdCl_2[P(Ph)_2CH_2CH_2CH_2P(Ph)_2]$, $PdCl_2[P(Ph)_2CH_2CH_2CH_2CH_2P(Ph)_2]$, $PdCl_2$ (dppf), and $PdCl_2[P(Ph)_3]_2$ where Ph represents phenyl group. Second examples are complex compounds prepared by substituting bromine atoms for chlorine atoms of the first examples. The method for preparing the complex compound is not particularly limited. It can be prepared by the method disclosed in V. D. Makhaev et al., Russian J. Coord. Chem. (Engl. Edit.) 22, 563–567 (1996). It is possible to prepare a complex compound by charging a reaction vessel with a compound containing a metal of 8, 9 and 10 groups of periodic table, a phosphine derivative, a solvent and the like, and then subjecting the resultant mixture to heating, stirring and the like. After that, the aromatic compound can be subjected to the carbonylation in the same reaction vessel.

In the invention, the metal of 8, 9 and 10 groups of periodic table is in an amount preferably of 0.00001–0.5 moles, more preferably of 0.00005–0.1 moles, still more preferably of 0.0001–0.1 moles, per mol of the aromatic compound. If it is less than 0.00001 moles, the reaction rate may become too low.

An amount greater than 0.5 moles of the metal is not an obstacle to the reaction, but may be uneconomical.

As stated above, the phosphine derivative, which is introduced in the form of free phosphine derivative or a ligand of the complex compound, is represented by the general formula $(R^1)_2P$—Q—$P(R^1)_2$ where $R^1$ is defined as above, and Q is a bivalent group such as an alkylene group represented by the general formula —$(CH_2)_m$— where m is an integer of 2–8.

Preferable examples of this phosphine derivative are 1,1'-bis(diphenylphosphino)ferrocene (dppf), 1,4-bis(diphenylphosphino)butane (dppb), 1,3-bis(diphenylphosphino)propane (dppp), and 1,2-bis(diphenylphosphino)ethane (dppe).

In addition to the phosphine derivative represented by the general formula (4), it is optional to add a phosphine derivative represented by the general formula (7) to the reaction system, $$P(L)_3 \qquad (7)$$

where each L is independently a lower alkyl group, phenyl group, or a substituted phenyl group having a lower alkyl substituent. It is preferable that this lower alkyl group has a carbon atom number of about 1–4. Nonlimitative examples of such phosphine derivative are triphenylphosphine, tri-o-tolylphosphine, tri-m-tolylphosphine, tri-p-tolylphosphine, tri-n-butylphosphine, and triethylphosphine.

First preferable examples of a combination of the metal compound and the first phosphine derivative, which are used as catalysts of the reaction, are (1) palladium chloride and dppb, (2) palladium chloride and dppp, (3) palladium acetate and dppb, (4) palladium acetate and dppp, (5) $PdCl_2$(dppe) and dppb, (6) $PdCl_2$(dppp) and dppb, (7) $PdCl_2$(dppb) and dppb, (8) $PdCl_2[P(Ph)_3]_2$ and dppb, (9) $PdCl_2$(dppe) and dppp, (10) $PdCl_2$(dppp) and dppp, (11) $PdCl_2$(dppb) and dppp, and (12) $PdCl_2[P(Ph)_3]_2$ and dppp. Second preferable examples are combinations of (a) the metal compounds prepared by substituting bromine atom(s) for chlorine atom (s) of the first preferable examples and (b) the respective first phosphine derivatives of the first preferable examples. The above combination of $PdCl_2$(dppb) and dppb is the most preferable example.

In the invention, the phosphine derivative, which is introduced in the form of free phosphine derivative or a ligand of palladium complex compound, is used in an amount preferably of 1–100 moles, more preferably of 1–50 moles, still more preferably of 1–20 moles, per mol of the metal of 8, 9 and groups of periodic table, in order to proceed the reaction. If it is less than 1 mol, the selectivity may not be improved. The addition of the phosphine derivative in an amount greater than 100 moles almost does not cause any adverse effects on the reaction rate, the yield and the like, but may be uneconomical. The above amount of the metal relative to that of the phosphine derivative is that of the metal contained in the reaction liquid. Thus, if the initial amount of the metal in the reaction liquid has decreased to a subsequent amount by the deposition of the metal due to a reaction analogous to the reaction of the invention, the above amount of the phosphine derivative may be adjusted based on the subsequent amount of the metal in the reaction liquid.

As mentioned above, it is particularly preferable to conduct the reaction in the presence of the above-mentioned complex compound, which is represented by the general formula $(L^1)_b(L^2)_aM$, and the phosphine derivative. The coexistence of these compounds can prevent the deposition of the metal (M) during the reaction. Therefore, it becomes possible to suppress the decrease of the actual concentration of the metal in the reaction liquid. This is a very important advantage in an industrial scale production of the benzoic acid derivative.

In the invention, the reaction may be conducted in a solvent or without using any solvent. It is possible to use the substrate itself as the solvent. Furthermore, it is possible to employ a conventional solvent used in a reaction in which carbon monoxide is used. Examples of such solvent are aliphatic hydrocarbons such as pentane, hexane, heptane and octane; aromatic hydrocarbons such as benzene, toluene and xylene; ethers such as diethyl ether, dioxane, tetrahydrofuran (THF) and ethylene glycol dimethyl ether; ketones such as acetone, methyl ethyl ketone and methyl isobutyl ketone; nitriles such as acetonitrile; tertiary amines such as pyridine; amides such as N,N-dimethylformamide (DMF) and N,N-dimethylacetamide (DMAc); and sulfur-containing compounds such as sulfolane. It should be noted that the hydroxy compound (i.e., water or an alcohol) is used as a reagent in the reaction. This hydroxy compound is capable of acting as a solvent. Therefore, it is not necessary to use any other solvent in the reaction. If such solvent is used, the volume of the entire reaction system may become too large. With this, it may be necessary to use a larger reaction vessel. Furthermore, the amount of the aimed product per batch may become too small.

As stated above, the hydroxy compound used in the reaction is represented by the general formula $R^2OH$ where $R^2$ is hydrogen or a straight-chain or branched alkyl group having a carbon atom number of 1–10. Examples of such alkyl group are methyl group, ethyl group, n-propyl group, iso-propyl group, n-butyl group, iso-butyl group, sec-butyl group, tert-butyl group, n-pentyl group, n-hexyl group, n-heptyl group, n-octyl group, n-nonyl group, and n-decyl group. Therefore, examples of the hydroxy compound are water and alcohols having the above alkyl groups. It suffices to use at least 1 mol of the hydroxy compound relative to 1 mol of the aromatic compound. In fact, it is preferable to add the hydroxy compound in a somewhat excessive amount relative to the aromatic compound. With this, it is possible to improve the conversion of the aromatic compound. Furthermore, the hydroxy compound can serve sufficiently as a solvent.

The base used in the invention can be selected from tertiary amines such as triethylamine, tripropylamine, tributylamine, triallylamine, N,N-dimethylaniline, N,N-diethylaniline, pyridine and N-methylmorpholine; acetates such as sodium acetate and potassium acetate; and inorganic bases such as sodium hydroxide, potassium hydroxide, sodium carbonate and potassium carbonate. The base is used in an amount preferably of 1.0–10.0 moles, more preferably of 1.0–5.0 moles, still more preferably of 1.0–3.0 moles, per mol of the aromatic compound. If it is less than 1.0 mol, the reaction may not proceed sufficiently. With this, the yield may become too low, and thus the reaction may become uneconomical.

Furthermore, it may become cumbersome to remove or collect the unreacted aromatic compound. An amount of greater than 10.0 moles of the base almost does not cause any change of the yield of the aimed benzoic acid derivative. This amount may, however, make a large amount of the base unreacted after the reaction. Therefore, it may be uneconomical and cumbersome to remove the unreacted base.

The method for producing the benzoic acid derivative may be as follows. At first, a reaction vessel is charged with the aromatic compound, the hydroxy compound (i.e., water or an alcohol), the metal compound, the phosphine, and the base. Then, the reaction vessel is closed. After that, the atmosphere of the reaction system is replaced with carbon monoxide. The reaction is conducted by heating the mixture with or without stirring under normal pressure (e.g., atmospheric pressure) or a pressurized condition. In fact, the carbon monoxide pressure is preferably from 1 to 100 $kg/cm^2$, more preferably from 1 to 50 $kg/cm^2$, still more preferably from 2 to 10 $kg/cm^2$. If it is lower than 1 $kg/cm^2$, the reaction may not proceed sufficiently. With this, the yield may become too low, making the reaction uneconomical, or it may take too much time to complete the reaction. Even if the pressure is adjusted to greater than 100 $kg/cm^2$, it almost does not bring any change in the reaction rate and the yield of the aimed benzoic acid derivative. Furthermore, it may become necessary to use a special pressure-tight reaction vessel. The reaction temperature is preferably from 30 to 200° C., more preferably from 50 to 180° C., still more preferably from 60 to 150° C. If it is lower than 30° C., the reaction may not proceed sufficiently. With this, the yield may become too low, making the reaction uneconomical, or it may take too much time to complete the reaction. If it is higher than 200° C., the reactant(s) may decompose during the reaction. With this, the yield may become too low, making the reaction uneconomical. Furthermore, it may become cumbersome to remove decomposition products.

The following nonlimitative complex compound preparation and examples are illustrative of the present invention. The examples were conducted with the following particulars. In the gas chromatographic analysis, FID was used as a detector. This analysis was conducted on the specimen prepared by methylesterifying carboxyl groups of the reaction product by a diazomethane treatment, unless otherwise stated. The results of the analysis are expressed in the areal percentage of each component, excluding solvent. The pressure is expressed in gauze pressure, unless otherwise stated.

Complex Compound Preparation

A complex compound, $PdCl_2(dppb)$, was prepared by a conventional method disclosed in Russian J. Coord. Chem. (Engl. Edit.), 22 (1996) 563–567, as follows. At first, 100 ml of acetonitrile was put into a 300 ml Erlenmeyer flask. Then, 0.574 g of palladium chloride was added to the flask. After that, the mixture was stirred with a stirrer, while heated at 70° C. in an oil bath. After dissolving the palladium chloride, 1.382 g of 1,4-bis(diphenylphosphino)butane was added to the flask. With this, pale yellow crystals precipitated. Then, stirring was continued for about 3 hr. After that, the crystals were separated from the solution by filtration and then washed with acetonitrile, thereby obtaining $PdCl_2(dppb)$.

By a method similar to the above, $PdCl_2(dppp)$ was prepared from palladium chloride and 1,3-bis(diphenylphosphino)propane (dppp).

EXAMPLE 1

At first, a 100 ml, pressure-tight, glass autoclave was charged with 11.24 g of 3,5-bis(trifluoromethyl) bromobenzene, 8.15 g of triethylamine, 5.62 g of water, 0.116 g of $PdCl_2(dppb)$ obtained in Complex Compound Preparation, and 0.082 g of 1,4-bis(diphenylphosphino) butane. Then, the atmosphere of the autoclave was replaced three times with carbon monoxide. Then, the reaction was conducted under a carbon monoxide pressure of 7.5 $kg/cm^2$ at 105° C. for 2.7 hr. After the reaction, the autoclave was cooled down to room temperature. Then, carbon monoxide was purged from the autoclave by replacing it a with nitrogen gas. The deposition of palladium black was not found in the reaction liquid, when the autoclave was opened. Then, 0.1 ml of the reaction liquid was sampled. Then, 5N hydrochloric acid was added to the sample to adjust its pH to less than 1. To this mixture 0.5 ml of diethyl ether was added, thereby extracting an organic component of the reaction liquid. The obtained ether phase was subjected to a diazomethane treatment and then to a gas chromatographic analysis. With this, the reaction product was found to contain 99.0% 3,5-bis(trifluoromethyl)benzoic acid and 0.4% 1,3-bis(trifluoromethyl)benzene. In this analysis, 3,5-bis(trifluoromethyl)bromobenzene was not detected.

EXAMPLE 2

At first, a 100 ml, pressure-tight, glass autoclave was charged with 11.24 g of 3,5-bis(trifluoromethyl) bromobenzene, 8.15 g of triethylamine, 5.62 g of water, 11.6 mg of $PdCl_2(dppb)$ obtained in Complex Compound Preparation, and 16.4 mg of 1,4-bis(diphenylphosphino) butane. Then, the atmosphere of the autoclave was replaced three times with carbon monoxide. Then, the reaction was conducted under a carbon monoxide pressure of 7.5 $kg/cm^2$ at 105° C. for 6 hr. Then, the same steps as those of Example 1 were conducted, thereby to obtain a specimen of a gas chromatographic analysis. When the autoclave was opened, the deposition of palladium black was not found in the reaction liquid. The reaction product was found by the gas chromatographic analysis to contain 97.5% 3,5-bis (trifluoromethyl)benzoic acid and 2.5% 3 5-bis (trifluoromethyl)bromobenzene. In this analysis, 1,3-bis (trifluoromethyl)benzene was not detected.

EXAMPLE 3

At first, a 100 ml, pressure-tight, glass autoclave was charged with 10.0 g of 3,5-bis(trifluoromethyl) bromobenzene, 3.80 g of triethylamine, 15 g of methanol, 10.3 mg of $PdCl_2(dppb)$ obtained in Complex Compound Preparation, and 14.6 mg of 1,4-diphenylphosphinobutane. Then, the atmosphere of the autoclave was replaced two times with carbon monoxide. Then, the reaction was conducted under a carbon monoxide pressure of 7.5 $kg/cm^2$ at 105° C. for 6 hr. Then, the same steps as those of Example 1 were conducted, except that the diazomethane treatment was omitted since the reaction product itself is in the form of methyl ester, thereby to obtain a specimen of a gas chromatographic analysis. The condition of the reaction liquid after the reaction was similar to that of Example 1. The reaction product was found by the gas chromatographic analysis to contain 99.5% methyl-3,5-bis(trifluoromethyl) benzoate and 0.1% 1,3-bis(trifluoromethyl)benzene. In this analysis, 3,5-bis(trifluoromethyl)bromobenzene was not detected.

EXAMPLE 4

At first, a 100 ml, pressure-tight, glass autoclave was charged with 11.24 g of 3,5-bis(trifluoromethyl) bromobenzene, 8.15 g of triethylamine, 5.62 g of water, 11.3 mg of $PdCl_2(dppp)$ obtained in Complex Compound Preparation, and 15.8 mg of 1,3-bis(diphenylphosphino) propane. Then, the atmosphere of the autoclave was replaced three times with carbon monoxide. Then, the reaction was conducted under a carbon monoxide pressure of 7.5 kg/cm$^2$ at 105° C. for 6 hr. Then, the same steps as those of Example 1 were conducted, thereby to obtain a specimen of a gas chromatographic analysis. The condition of the reaction liquid after the reaction was similar to that of Example 1. The reaction product was found by the gas chromatographic analysis to contain 98.5% 3,5-bis(trifluoromethyl) benzoic acid and 1.5% 3,5-bis(trifluoromethyl) bromobenzene. In this analysis, 1,3-bis(trifluoromethyl) benzene was not detected.

EXAMPLE 5

At first, a 100 ml, pressure-tight, glass autoclave was charged with 12.57 g of 2-chloro-3, 5-bis(trifluoromethyl) bromobenzene, 8.15 g of triethylamine, 5.62 g of water, 11.6 mg of PdCl$_2$(dppb) obtained in Complex Compound Preparation, and 16.4 mg of 1,4-bis(diphenylphosphino) butane. Then, the atmosphere of the autoclave was replaced three times with carbon monoxide. Then, the reaction was conducted under a carbon monoxide pressure of 7.5 kg/cm$^2$ at 105° C. for 6 hr. Then, the same steps as those of Example 1 were conducted, thereby to obtain a specimen of a gas chromatographic analysis. When the autoclave was opened, the deposition of palladium black was not found in the reaction liquid. The reaction product was found by the gas chromatographic analysis to contain 23.2% 2-chloro-3,5-bis (trifluoromethyl)benzoic acid, the unreacted raw material (i.e., 2-chloro-3,5-bis(trifluoromethyl)bromobenzene), and others. Furthermore, the ether phase prior to the diazomethane treatment was subjected to a GC-mass-spectrographic analysis. In this analysis, a component of the specimen was identified as 2-chloro-3,5-bis(trifluoromethyl) benzoic acid, as follows: M/Z: 292;294 (intensity ratio 10:3: parent peak), 275;277 (intensity ratio 10:3), 247;249 (intensity ratio 10:3) 228;230 (intensity ratio 10:3)

EXAMPLE 6

At first, a 1-liter stainless steel autoclave was charged with 416 g of 3,5-bis(trifluoromethyl)bromobenzene (purity: 97.4%), 302 g of triethylamine, 208 g of water, 0.429 g of PdCl$_2$(dppb) obtained in Complex Compound Preparation, and 0.605 g of 1,4-bis(diphenylphosphino)butane. Then, the atmosphere of the autoclave was replaced three times with carbon monoxide. Then, the reaction was conducted under a carbon monoxide pressure of 7.5 kg/cm$^2$ at 105° C. for 6 hr. Then, the same steps as those of Example 1 were conducted, thereby to obtain a specimen of a gas chromatographic analysis. The condition of the reaction liquid after the reaction was similar to that of Example 1. The reaction product was found by the gas chromatographic analysis to contain 97.4% 3,5-bis(trifluoromethyl)benzoic acid and 0.2% 3,5-bis(trifluoromethyl)bromobenzene. In this analysis, 1,3-bis(trifluoromethyl)benzene was not detected.

Furthermore, hydrochloric acid was added to the rest of the reaction mixture in order to adjust its pH to lower than 1. Then, the precipitated solid was collected, then washed with water, and then dried. With this, 333.5 g of 3,5-bis (trifluoromethyl)benzoic acid (purity>99%) was obtained. The actual yield of this product was 93.4%.

EXAMPLE 7

At first, a 100 ml, pressure-tight, glass autoclave was charged with 11.24 g of 3,5-bis(trifluoromethyl) chlorobenzene, 9.60 g of triethylamine, 6.61 g of water, 13.65 mg of PdCl$_2$(dppb) obtained in Complex Compound Preparation, and 48.22 mg of 1,4-bis(diphenylphosphino) butane. Then, the atmosphere of the autoclave was replaced three times with carbon monoxide. Then, the reaction was conducted under a carbon monoxide pressure of 10 kg/cm$^2$ at 130° C. for 10 hr. Then, the same steps as those of Example 1 were conducted, thereby to obtain a specimen of a gas chromatographic analysis. The condition of the reaction liquid after the reaction was similar to that of Example 1. The reaction product was found by the gas chromatographic analysis to contain 66.1% of 3,5-bis (trifluoromethyl)benzoic acid, 0.4% of 1,3-bis (trifluoromethyl)benzene, and 33.5% of the unreacted 3,5-bis(trifluoromethyl)chlorobenzene.

EXAMPLE 8

At first, a 100 ml, pressure-tight, glass autoclave was charged with 13.00 g of 3,5-bis(trifluoromethyl) bromobenzene, 9.42 g of triethylamine, 6.49 g of water, 3.94 mg of palladium chloride, and 37.86 mg of 1,4-bis (diphenylphosphino)butane. Then, the atmosphere of the autoclave was replaced two times with carbon monoxide. Then, the autoclave was maintained at 65° C. for 2 hr. Then, the reaction was conducted under a carbon monoxide pressure of 7.5 kg/cm$^2$ at 105° C. for 6.0 hr. When the autoclave was cooled down to room temperature after the reaction, palladium black was found in the reaction liquid. Then, a cooled 2N-NaOH was added to the reaction liquid to adjust its pH to not lower than 11. Then, an insoluble matter of the mixture was separated by filtration. Then, a small amount of the obtained filtrate was taken and then adjusted to having a pH of not higher than 1. To the resultant mixture diethyl ether was added, in order to extract an organic component from the mixture. Then, the obtained ether phase was subjected to a diazomethane treatment, to prepare a specimen of a gas chromatographic analysis. The reaction product was found by the gas chromatographic analysis to contain 50.3% 3,5-bis(trifluoromethyl)benzoic acid, 0.10% 1,3-bis (trifluoromethyl)benzene, and 49.1% 3,5-bis (trifluoromethyl)bromobenzene.

Comparative Example 1

At first, a 100 ml, pressure-tight, glass autoclave was charged with 11.24 g of 3,5-bis(trifluoromethyl) bromobenzene, 8.14 g of triethylamine, 5.62 g of water, 43.08 mg of palladium acetate, and 150.9 mg of triphenylphosphine. Then, the atmosphere of the autoclave was replaced three times with nitrogen. Then, the reaction was conducted under a nitrogen pressure of 7.5 kg/cm$^2$ at 105° C. for 6 hr. When the autoclave was cooled down to room temperature after the reaction, palladium black was found in the reaction liquid. Then, the same steps as those of Example 1 were conducted, thereby to obtain a specimen of a gas chromatographic analysis. The reaction product was found by the gas chromatographic analysis to contain 82% 3,5-bis (trifluoromethyl)benzoic acid and 16% 1,3-bis (trifluoromethyl)benzene. In this analysis, 3,5-bis (trifluoromethyl)bromobenzene was not detected.

Comparative Example 2

At first, a 100 ml, pressure-tight, glass autoclave was charged with 11.24 g of 3,5-bis(trifluoromethyl) bromobenzene, 8.14 g of triethylamine, 5.62 g of water, 34.02 mg of palladium chloride, and 150.9 mg of triphenylphosphine. Then, the atmosphere of the autoclave was replaced three times with nitrogen. Then, the reaction was conducted under a nitrogen pressure of 7.5 kg/cm² at 105° C. for 6 hr. When the autoclave was cooled down to room temperature after the reaction, palladium black was found in the reaction liquid. Then, the same steps as those of Example 1 were conducted, thereby to obtain a specimen of a gas chromatographic analysis. This specimen was found by the gas chromatographic analysis to contain 24% 3,5-bis (trifluoromethyl)benzoic acid, 3% 1,3-bis(trifluoromethyl) benzene, and 71% 3,5-bis(trifluoromethyl)bromobenzene.

The entire disclosure of japanese patent application no. 10–343402 filed on Dec. 2, 1998, of which priority is claimed in the application, including specification, claims, and summary, is incorporated herein by reference in its entirety:

What is claimed is:

1. A method for producing a benzoic acid derivative represented by the general formula (1), said method comprising reacting an aromatic compound represented by the general formula (2), with carbon monoxide and a hydroxy compound represented by the general formula (3), in the presence of (a) a metal compound containing a metal of 8, 9 and 10 groups of periodic table, (b) a first phosphine derivative represented by the general formula (4), and (c) a base,

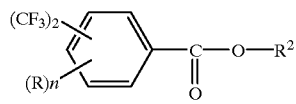

(1)

where R is trifluoromethyl group, trifluoromethyloxy group, a halogen that is fluorine, chlorine, bromine or iodine, nitro group, acetyl group, cyano group, an alkyl group having a carbon atom number of 1–4, an alkoxyl group having a carbon atom number of 1–4, or an alkoxycarbonyl group having a carbon atom number of 2–5; R² is hydrogen or an alkyl group having a carbon atom number of 1–10; and n is an integer of 0–3,

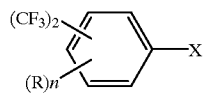

(2)

where X is a halogen as defined above, trifluoromethanesulfonate group, an alkylsulfonate group having a carbon atom number of 1–4, or a substituted or unsubstituted arylsulfonate group; and R and n are defined as above,

 (3)

where R² is defined as above,

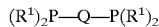 (4)

where each R¹ is independently phenyl group, o-methylphenyl group, m-methylphenyl group, or p-methylphenyl group; and Q is a bivalent group.

2. A method according to claim 1, wherein said X in the general formula (2) is said halogen.

3. A method according to claim 1, wherein said X in the general formula (2) is bromine or iodine, and said R in the general formulas (1) and (2) is said halogen.

4. A method according to claim 1, wherein said aromatic compound is a halogeno-bis(trifluoromethyl)benzene represented by the general formula (5),

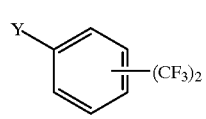

(5)

where Y is bromine or iodine.

5. A method according to claim 1, wherein said aromatic compound is 3,5-bis(trifluoromethyl)bromobenzene, 3,5-bis (trifluoromethyl)iodobenzene, or 2-chloro-3,5-bis (trifluoromethyl)bromobenzene.

6. A method according to claim 1, wherein said hydroxy compound is water, methanol, or ethanol.

7. A method according to claim 1, wherein said Q of the general formula (4) is an alkylene group represented by the general formula —(CH$_2$)$_m$— where m is an integer of 2–8.

8. A method according to claim 1, wherein said first phosphine derivative is 1,3-bis(diphenylphosphino)propane or 1,4-bis(diphenylphosphino)butane.

9. A method according to claim 1, wherein said metal of said metal compound is selected from the group consisting of iron, cobalt, palladium, platinum, rhodium, ruthenium, iridium, and osmium.

10. A method according to claim 9, wherein said metal is palladium.

11. A method according to claim 1, wherein said metal compound is palladium chloride or palladium acetate.

12. A method according to claim 1, wherein said metal compound is a complex compound represented by the general formula (6), $$(L^1)_b(L^2)_a M \quad (6)$$

where L¹ is a second phosphine derivative represented by the general formula (4) or a third phosphine derivative represented by the general formula (7); L² is a ligand selected from the group consisting of chlorine, bromine, iodine, S, NO, CO, CH$_3$COO—, cyclopentadienyl, cyclooctadiene, and diphenylacetylene; M is a metal of 8, 9 and 10 groups of periodic table; a total of "a" and "2b" equals to a coordination number of "M" when L¹ is a bidentate ligand; and a total of "a" and "b" equals to said coordination number of "M" when L¹ is a monodentate ligand,

 (4)

where R¹ and Q are defined as above,

 (7)

where each L is independently a lower alkyl group, phenyl group, or a substituted phenyl group having a lower alkyl substituent.

13. A method according to claim 12, wherein said M of the general formula (6) is palladium.

14. A method according to claim 12, wherein said Q of the general formula (4) is an alkylene group represented by the general formula —(CH$_2$)$_m$— where m is an integer of 2–8.

15. A method according claim 12, wherein said complex compound is
dichloro[1,4-butanediylbis(diphenylphosphine)P,P'] palladium,
dichloro [1,3-propanediylbis(diphenylphosphine)P,P'] palladium
or dichlorobis(triphenylphosphino)palladium.

16. A method according to claim 1, wherein said metal compound is
dichloro[1,4-butanediylbis(diphenylphosphine)P,P'] palladium,
and said first phosphine derivative is 1,4-bis(diphenylphosphino)butane.

17. A method according to claim 1, wherein said reacting is conducted in a condition that a total amount of said first phosphine derivative, which is introduced in the form of free phosphine derivative or a ligand of palladium complex compound, is 1 to 100 moles per mol of said metal of said metal compound.

18. A method according to claim 1, wherein said metal is in an amount of 0.00001–0.5 moles per mol of said aromatic compound.

19. A method according to claim 1, wherein said base is in an amount of 1.0–10.0 moles per mol of said aromatic compound.

20. A method according to claim 1, wherein said reacting is conducted in an atmosphere consisting essentially of said carbon monoxide having a pressure of 1–100 kg/cm$^2$.

21. A method according to claim 1, wherein said reacting is conducted at a temperature of 30–200° C.

22. 2-chloro-3,5-bis(trifluoromethyl)benzoic acid.

* * * * *